United States Patent [19]

Dorn et al.

[11] 4,064,236

[45] Dec. 20, 1977

[54] PEPTIDE CARBAZATES AND PHARMACEUTICAL COMPOSITION

[75] Inventors: Conrad P. Dorn, Plainfield; Shu S. Yang, Piscataway, both of N.J.

[73] Assignee: Merck & Co., Inc., Rahway, N.J.

[21] Appl. No.: 643,721

[22] Filed: Dec. 23, 1975

[51] Int. Cl.$^2$ .................... A61K 37/00; C07C 103/52; A61K 37/02
[52] U.S. Cl. .............................. 424/177; 260/112.5 R
[58] Field of Search .................. 260/112.5 R; 420/177

[56] References Cited

U.S. PATENT DOCUMENTS

| | | | |
|---|---|---|---|
| 3,888,840 | 6/1975 | Failli et al. | 260/112.5 R |
| 3,904,593 | 9/1975 | Immer et al. | 260/112.5 R |

*Primary Examiner*—Delbert R. Phillips
*Attorney, Agent, or Firm*—Raymond M. Speer; Harry E. Westlake; Frank M. Mahon

[57] ABSTRACT

Certain novel peptide carbazates, their preparation, pharmaceutical compositions and novel methods of treating pancreatitis.

9 Claims, No Drawings

PEPTIDE CARBAZATES AND PHARMACEUTICAL COMPOSITION

BACKGROUND OF THE INVENTION

This invention relates to a novel class of peptide carbazates useful for selectively inhibiting elastase, a proteolytic enzyme. Certain clinical symptoms found in pancreatitis, emphysema and rheumatoid arthritis are believed to be caused by uncontrolled elastase in the affected tissues.

It is an object of this invention to provide a novel group of elastase inhibitors useful for treating pancreatitis. Another object of this invention is to provide a novel group of enzyme inhibitors which will selectively react with elastase.

DETAILED DESCRIPTION OF THE INVENTION

We have found that certain peptide carbazates will selectively inhibit elastase by blocking the enzyme. These peptide carbazates may be used to treat pancreatitis. The novel peptide carbazates of this invention have the following structural formula:

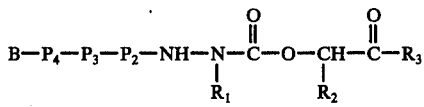

wherein
- B is $C_{1-5}$alkanoyl (such as acetyl), t-butoxycarbonyl or carbobenzyloxy,
- $P_4$ is alanyl or prolyl,
- $P_3$ is alanyl,
- $P_2$ is prolyl or leucyl,
- $R_1$ is $C_{1-5}$alkyl,
- $R_2$ methyl, benzyl or 4-aminobutyl, and
- $R_3$ is hydroxy, $C_{1-5}$alkoxy (such as methoxy or ethoxy), amino, N-$C_{1-5}$alkylamino (such as N-methylamino), N,N-di($C_{1-5}$alkyl)amino (such as N,N-dimethylamino), N-benzylamino, N-phenylamino, hydrazino, substituted hydrazino (such as methylhydrazino, ethylhydrazino, phenylhydrazino and benzylhydrazino, benzyloxy, substituted benzyloxy (such as p-iodobenzyloxy) or

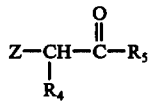

wherein
- $R_4$ is methyl or benzyl, and
- $R_5$ is hydroxy, $C_{1-5}$alkoxy (such as methoxy or ethoxy), amino, N-$C_{1-5}$alkylamino (such as N-methylamino), N,N-di($C_{1-5}$alkyl)amino, N-benzylamino, N-phenylamino, hydrazino, benzyloxy or substituted benzyloxy (such as p-iodobenzyloxy), and
- Z is —NH— or —O—.

In a preferred embodiment, B is $C_{1-5}$alkanoyl, $R_1$ is methyl or isopropyl, $R_2$ is methyl or benzyl, and $R_3$ is $C_{1-5}$alkoxy, benzyloxy, substituted benzyloxy, amino, hydrazino, N-phenylamino, N-benzylamino or $C_{1-5}$alkylamino.

In a more preferred embodiment, B is acetyl, $P_2$ is prolyl, $R_1$ is methyl, $R_2$ is methyl and $R_3$ is benzyloxy, p-iodobenzyloxy, amino, hydrazino, N-phenylamino, N-benzylamino or N-methylamino.

The following novel compounds are representative of the invention:

Acetylprolylalanylprolyl-2-azaalanyl-dl-lactamide,
Acetylalanylalanylprolyl-2-azaalanyl-dl-lactamide,
Acetylalanylalanylprolyl-2-azaalanyl-l-lactic acid benzyl ester,
Acetylalanylalanylprolyl-2-azaalanyl-l-lactic acid p-iodobenzyl ester,
Acetylalanylalanylprolyl-2-azaalanyl-N-benzyl-l-lactamide,
Acetylalanylalanylprolyl-2-azaalanyl-N-methyl-l-lactamide,
Acetylalanylalanylprolyl-2-azaalanyl-l-lacthydrazide,
Acetylalanylalanylprolyl-2-azaalanyl-N-phenyl-l-lactamide,
Acetylprolylalanylprolyl-2-azavalyl-dl-lactamide,
Acetylalanylalanylprolyl-2-azavalyl-dl-lactamide,
Acetylalanylalanylprolyl-2-azavalyl-l-lactic acid benzyl ester,
Acetylalanylalanylprolyl-2-azavalyl-l-lactic acid p-iodobenzyl ester,
Acetylalanylalanylprolyl-2-azavalyl-N-benzyl-l-lactamide,
Acetylalanylalanylprolyl-2-azavalyl-N-methyl-l-lactamide,
Acetylalanylalanylprolyl-2-azavalyl-l-lacthydrazide,
Acetylalanylalanylprolyl-2-azavalyl-N-phenyl-l-lactamide,
Acetylprolylalanylprolyl-2-azaalanyl-dl-α-(4-aminobutyl)-glycolamide,
Acetylalanylalanylprolyl-2-azaalanyl-dl-α-(4-aminobutyl)-glycolamide,
Acetylalanylalanylprolyl-2-azaalanyl-l-α-(4-aminobutyl)-glycolic acid benzyl ester,
Acetylalanylalanylprolyl-2-azaalanyl-l-α-(4-aminobutyl)-glycolic acid p-iodobenzyl ester,
Acetylalanylalanylprolyl-2-azaalanyl-N-benzyl-l-α-(4-aminobutyl)-glycolamide,
Acetylalanylalanylprolyl-2-azaalanyl-N-methyl-l-α-(4-aminobutyl)-glycolamide,
Acetylalanylalanylprolyl-2-azaalanyl-l-α-(4-aminobutyl)-glycolhydrazide,
Acetylalanylalanylprolyl-2-azaalanyl-N-phenyl-lα-(4-aminobutyl)-glycolamide,
Acetylprolylalanylprolyl-2-azavalyl-dl-α-(4-aminobutyl)-glycolamide,
Acetylalanylalanylprolyl-2-azavalyl-dl-α-(4-aminobutyl)-glycolamide,
Acetylalanylalanylprolyl-2-azavalyl-l-α-(4-aminobutyl)-glycolic acid benzyl ester,
Acetylalanylalanylprolyl-2-azavalyl-l-α-(4-aminobutyl)-glycolic acid p-iodobenzyl ester,
Acetylalanylalanylprolyl-2-azavalyl-N-benzyl-l-α-(4-aminobutyl)-glycolamide,
Acetylalanylalanylprolyl-2-azavalyl-N-methyl-l-α-(4-aminobutyl)-glycolamide,
Acetylalanylalanylprolyl-2-azavalyl-l-α-(4-aminobutyl)-glycolhydrazide and
Acetylalanylalanylprolyl-2-azavalyl-N-phenyl-l-α-(4-aminobutyl)-glycolamide.

Another aspect of this invention relates to the novel pharmaceutical compositions for treating pancreatitis, comprising a non-toxic pharmaceutically acceptable carrier and a compound of formula I, supra, wherein B, $P_4$, $P_3$, $P_2$, $R_1$, $R_2$ and $R_3$ are as defined above.

The non-toxic pharmaceutically acceptable carrier may be, for example, either a solid or a liquid. Exemplary of solid carriers are lactose, corn starch, gelatin, talc, stereotix, stearic acid, magnesium stearate, terra alba, sucrose, agar, pectin, acacia and carboxymethylcellulose (CMC). Exemplary of liquid carriers are peanut oil, olive oil, sesame oil, ethyl alcohol, glycerin and water. Similarly, the carrier or diluent may contain a time delay material, such as glyceryl monostearate or glyceryl distearate, alone or with a wax.

Several pharmaceutical forms of the therapeutically useful compositions may be used. For example, if a solid carrier is used, the compositions may take the form of tablets, capsules, powders, troches or lozenges, prepared by standard pharmaceutical techniques. If a liquid carrier is used the preparation may be in the form of a soft gelatin, syrup, a liquid solution, a liquid emulsion or a liquid suspension. The liquid may be sprayed by aerosol or nebulizer. Suppositories may be prepared in the conventional manner by mixing the compounds of this invention with a suitable non-irritating excipient which is solid at room temperature. Exemplary of excipients are cocoa butter and polyethylene glycol. Gels, lotions and aerosol sprays for topical application may be prepared in conventional manners.

The active compounds are orally, or parenterally administered in the therapeutically effective amount to treat pancreatitis. Advantageously, the active compounds will be administered, alone, or in a pharmaceutical composition in an amount of from about 1.0 mg to 100 mg per kg body weight per day (50 mg to 5.0 g per patient per day) of the active compound preferably from about 1.5 to 15 mg per kilogram body weight per day. The daily dosage may be given in either single or multiple dosages.

Another aspect of this invention is the method of treating pancreatitis by administering to a patient (animal or human) a compound of formula I, supra, admixed with a non-toxic pharmaceutical carrier such as exemplified above. In addition, the compounds of formula I, supra, wherein B, $P_4$, $P_3$, $P_2$ and $R_1$ are defined above and $R_2$ is methyl and $R_3$ is amino, hydrazino, N-benzylamino, N-methylamino or N-phenylamino may be used to treat emphysema and/or rheumatoid arthritis as well as pancreatitis, using the same dosage range as for pancreatitis. It should be understood that although preferred dosage ranges are given the dose level for any particular patient depends on the activity of the specific compound employed. Also many other factors that modify the actions of drugs will be taken into account by those skilled in the art in the therapeutic use of medicinal agents, particularly those described above; for example, body weight, sex, diet, time of administration, route of administration, rate of excretion, drug combination, reaction sensitivities and severity of the particular disease.

Another aspect of this invention is the process for preparing the novel compounds of formula I, supra, wherein B, $P_4$, $P_3$, $P_2$, $R_1$, $R_2$ and $R_3$ are as defined above by reacting a compound of formula II, $$B—P_4—P_3—P_2—X \qquad II$$

with a compound of formula III,

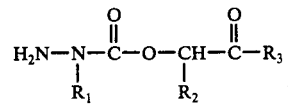

wherein X is hydroxy, halo, p-nitrophenoxy, $—O—P_2—P_3—P_4—B$ or

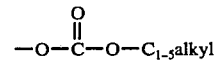

and B, $P_4$, $P_3$, $P_2$, $R_1$, $R_2$ and $R_3$ are defined above. It is preferred to carry the reaction out in an inert solvent. The solvent is not critical. Examples of suitable solvents are ethers (such as tetrahydrofuran (THF)), halogenated hydrocarbons (such as chloroform), and $C_{1-3}$ alkanoyl nitriles (such as acetonitrile). The reaction temperature is generally about $-20°$ to $100°$ C preferably $-20°$ to $+20°$ C and in the case of mixed anhydrides, $-20°$ to $0°$ C. The time of reaction is not critical and generally the reaction is carried out until it is essentially complete. The pressure is not critical and generally the reaction is carried out at atmospheric pressure in an open system. When X is halo, the reaction may be carried out in the presence of an acid acceptor (such as pyridine). The product of the reaction, compounds of formula I, may be recovered in the conventional manner, such as by filtration and evaporation of the filtrate to yield the compound of formula I. The compound of formula I may be purified by chromatographing it on a silica gel column using a solvent system such as methanol in chloroform.

The following examples are given to illustrate the invention and are not intended to limit it in any manner. All parts are given in parts by weight unless otherwise expressed. All temperatures are given in degrees centigrade (° C) unless otherwise expressed.

EXAMPLE 1

Acetylprolylalanylprolyl-2-azaalanyl-l-lactic acid ethyl ester

Step A — Preparation of (l-ethoxycarbonyl)-ethyl chloroformate

To a stirred solution of phosgene in benzene (0.12 mole) at 0° to 5° is added a solution of ethyl 1-(+)-lactate (0.1 mole) in dry tetrahydrofuran (100 ml) containing triethylamine (0.105 mole) over a period of 1 hour. The mixture is stirred at 0° to 5° for ½ hour and at room temperature for 1 hour. The mixture is filtered and the filtrate is concentrated in vacuo to give (L-ethoxycarbonyl)-ethyl chloroformate.

Step B — Preparation of 2-azaalanyl-l-lactic acid ethyl ester

To a stirred solution of methylhydrazine (0.126 mole) in dry tetrahydrofuran containing triethylamine (0.105 mole) at 0° to 5° is added a solution of (l-ethoxycarbonyl)ethyl chloroformate (0.067 mole) in tetrahydrofuran (50 ml) over a period of 1 hour. After the addition, the mixture is stirred at 0° to 5° for 1 hour and at room temperature overnight. The precipitate is filtered off, and the filtrate is concentrated to dryness. Chromatography on silica gel (270 gm) and elution with 2% methanol in chloroform gives 2-azaalanyl-l-lactic acid ethyl ester.

Step C — Preparation of acetylprolylalanylprolyl-2-azaalanyl-l-lactic acid ethyl ester Acetylprolylalanylproline (2 mmole) is dissolved in methylene chloride (5 ml) containing N-methylmorpholine (2 mmole) and diluted with dry tetrahydrofuran (400 ml). To this stirred solution at −20° to −25° is added isobutyl chloroformate (2 mmole) and the mixture is stirred for 15 minutes. A solution of 2-azaalanyl-l-lactic acid ethyl ester (2 mmole) in tetrahydrofuran (2 ml) is then added. The mixture is allowed to warm to room temperature over a period of 1 hour and stirred for a further 3 hours. The mixture is filtered, and the filtrate is evaporated to dryness. Chromatography on silica gel (38 gm) and elution with 5% methanol in chloroform gives acetylprolylalanylprolyl-2-azaalanyl-l-lactic acid ethyl ester.

EXAMPLE 2

Acetylalanylalanylprolyl-2-azaalanyl-l-lactic acid ethyl ester

To a stirred solution of acetylalanylalanylproline (0.66 mole) and N-methylmorpholine (0.66 mole) in dry tetrahydrofuran (25 ml) at −20° to −25° is added isobutylchloroformate (0.66 mmole). After 10 minutes a solution of 2-azaalanyl-l-lactic acid ethyl ester (0.66 mmole, example 3, step B) in tetrahydrofuran (2 ml) is added dropwise and the mixture is allowed to warm to room temperature over a period of 1 hour and stirred for a further 3 hours. The precipitate is removed by filtration, and the filtrate is concentrated to dryness. Chromatography of the residue on a silica gel (30 gm) and elution with 8% methanol in chloroform yields acetylalanylalanylprolyl-2-azaalanyl-l-lactic acid ethyl ester.

EXAMPLE 3

Acetylprolylalanylprolyl-2-azaalanyl-dl-lactic acid ethyl ester

Employing the procedure substantially as described in Example 1, but substituting for the ethyl 1-(+)-lactate used in Step A thereof, an equivalent amount of ethyl dl-lactate, there are prepared in sequence, Step A — (1-ethoxycarbonyl)-ethyl chloroformate.
Step B — 2-azaalanyl-dl-lactic acid ethyl ester.
Step C — acetylprolylalanylprolyl-2-azaalanyl-dl-lactic acid ethyl ester.

EXAMPLE 4

Acetylprolylalanylprolyl-2-azaalanyl-dl-lactamide

Acetylprolylalanylprolyl-2-azaalanyl-dl-lactic acid ethyl ester (0.011 mole) is treated with liquid ammonia (130 ml) in a bomb at room temperature for 24 hours. The reaction mixture is evaporated to dryness and the residue is purified by chromatography on silica gel (275 gm) and elution with 14% methanol in chloroform to give acetylprolylanylpropyl-2-azaalanyl-dl-lactamide.

EXAMPLE 5

Acetylalanylalanylpropyl-2-azaalanyl-dl-lactamide

Step A — Preparation of 2-azaalanyl-dl-lactic acid ethyl ester

Following the procedure of Example 1, Step A and Step B, but substituting an equivalent amount of ethyl dl-lactate for the ethyl 1-(+)-lactate used thereof, there is produced 2-azaalanyl-dl-lactic acid ethyl ester.

Step B — Preparation of 2-azaalanyl-dl-lactamide

2-Azaalanyl-dl-lactic acid ethyl ester (0.02 mole) is treated with liquid ammonia (50 ml) at room temperature for 16 hours. The mixture is evaporated to dryness. Chromatography on silica gel (80 gm) and elution with 15% methanol in chloroform gives 2-azaalanyl-dl-lactamide.

Step C — Preparation of acetylalanylalanylprolyl-2-azaalanyl-dl-lactamide

Acetylalanylalanylproline (2 mmole) and N-methylmorpholine (2 mmole) are dissolved in dry tetrahydrofuran (200 ml) and cooled to −20° to −25°. Isobutyl chloroformate (2 mmole) is added, and the mixture is stirred at −20° for 10 minutes. A solution of 2-azaalanyl-dl-lactamide (2 mmole) in tetrahydrofuran (10 ml) is added dropwise, and the mixture is allowed to warm to room temperature over a period of 2 hours and stirred for a further 3 hours. The precipitate is filtered off and the filtrate is evaporated to dryness. Chromatography of the residue on silica gel (70 gm) and elution with 18% methanol in chloroform gives acetylalanylalanylprolyl-2-azaalanyl-dl-lactamide.

EXAMPLE 6

Acetylalanylalanylleucyl-2-azaalanyl-dl-lactic acid ethyl ester

Step A — Preparation of N-tert-butoxycarbonylalanylleucine benzyl ester

To a solution of N-tert-butoxycarbonylalanine (0.06 mole) and N-methylmorpholine (0.06 mole) in dry tetrahydrofuran (100 ml) at −20° to −25° is added isobutyl chloroformate (0.06 mole) with stirring. After 10–15 minutes, a solution of leucine benzyl ester (0.06 mole) and N-methylmorpholine (6.8 ml) in methylene chloride-tetrahydrofuran (1:1, 100 ml) is added over a period of ½ hour. The mixture is allowed to warm to room temperature and stirred at room temperature overnight. The resulting mixture is concentrated in vacuo and the residue extracted between chloroform and dilute hydrochloric acid. The chloroform layer is separated, washed with water, dried over sodium sulfate and concentrated to give the crude N-tert-butoxycarbonylalanylleucine benzyl ester to be used as in the next step.

Step B — Preparation of alanylleucine benzyl ester hydrochloride

To a solution of the crude product obtained above (ca. 0.04 mole) in ethyl acetate (250 ml) at 0° to 5° is carefully passed a slow stream of dry hydrogen chloride gas for 1 hour. The solution is concentrated in vacuo to give the crude alanylleucine benzyl ester hydrochloride.

Step C — Preparation of acetylalanylalanylleucine benzyl ester

To a stirred solution of acetylalanine (0.03 mole) and N-methylmorpholine (0.03 mole) in dry tetrahydrofuran (200 ml) at −20° to −25° is added isobutyl chloroformate (0.03 mole). After 10 minutes, a suspension of the crude alanylleucine benzyl ester hydrochloride (0.03+ mole) and N-methylmorpholine (0.04 mole) in tetrahydrofuran (25 ml) is added in portions over ½ hour. The mixture is allowed to warm to room temperature over a period of 2 hours and stirred overnight. The reaction mixture is evaporated to dryness and the residue is purified by chromatography on silica gel (200 gm) and elution with 10% methanol in chloroform to give acetylalanylalanylleucine benzyl ester.

Step D — Preparation of acetylalanylalanylleucine

Acetylalanylalanylleucine benzyl ester (2 mmole) is dissolved in denaturated ethyl alcohol (0.5 gal. benzene added to 100 gal. of absolute ethanol) (15 ml) and hydrogenated over 10% palladium/charcoal (0.1 gm) at 40 psi for ½ hour. The solution was filtered through Celite and evaporated in vacuo. The residue is triturated with diethyl ether to give crystalline acetylalanylalanylleucine, m.p. 185°–186°.

Step E — Preparation of acetylalanylalanylleucyl-2-azaalanyl-dl-lactic acid ethyl ester Acetylalanylalanylleucine (1.5 mmole) and N-methylmorpholine (3 mmole) are dissolved in methylene chloride (10 ml) and diluted with dry tetrahydrofuran (250 ml) and cooled to −20° to −25°. Isobutyl chloroformate (1.5 mmole) is added with stirring and the mixture is stirred for 10 minutes. A solution of 2-azaalanyl-dl-lactic acid ethyl ester (1.5 mmole, Example 5, Step A) in tetrahydrofuran (3 ml) is added and the mixture is allowed to warm to room temperature over a period of 2 hours and stirred overnight. The precipitate is filtered off and the filtrate is evaporated to dryness. Chromatography on silica gel (25 gm) and elution with 12% methanol in chloroform gives acetylalanylalanylleucyl-2-azaalanyl-dl-lactic acid ethyl ester.

EXAMPLE 7

Acetylprolylalanylleucyl-2-azaalanyl-dl-lactic acid ethyl ester

Employing the procedure substantially as described in Example 6, but substituting for the acetylalanine used in Step C thereof, an equivalent amount of acetylproline, there are prepared in sequence, Step C — acetylprolylalanylleucine benzyl ester.
Step D — acetylprolylalanylleucine.
Step E — acetylprolylalanylleucyl-2-azaalanyl-dl-lactic acid ethyl ester.

EXAMPLE 8

Acetylalanylalanylprolyl-2-azaalanyl-1-3-phenyllactic acid ethyl ester

Step A — Preparation of ethyl 1-(−)-3-phenyllactate

A solution of 1-(−)-3-phenyllactic acid (12 mmole) in absolute ethanol (150 ml) at 0°–5° is saturated with a slow stream of dry hydrogen chloride gas until the exothermic reaction ceases (ca. 1 hour). The solution is concentrated in vacuo to give the crude ethyl 1-3-phenyllactate.

Step B — Preparation of (1-ethoxycarbonyl)-2-phenylethyl chloroformate

Following the procedure of Example 1, Step A, but substituting an equivalent amount of ethyl-(−)-3-phenyllactate for the ethyl 1-(+)-lactate used therein, there is produced (1-ethoxycarbonyl)-2-phenylethyl chloroformate.

Step C — Preparation of 2-azaalanyl-1-3-phenyllactic acid ethyl ester

Following the procedure of Example 1, Step B, but substituting an equivalent amount of (1-ethoxycarbonyl)-2-phenylethyl chloroformate for the (1-ethoxycarbonyl)-ethyl chloroformate used therein, there is produced 2-azaalanyl-1-3-phenyllactic acid ethyl ester.

Step D — Preparation of acetylalanylalanylprolyl-2-azaalanyl-1-3-phenyllactic acid ethyl ester Following the procedure of Example 2, but substituting an equivalent amount of 2-azaalanyl-1-3-phenyllactic acid ethyl ester for the 2-azaalanyl-1-lactic acid ethyl ester used herein, there is obtained acetylalanylalanylprolyl-2-azaalanyl-1-3-phenyllactic acid ethyl ester.

EXAMPLE 9

Acetylalanylalanylprolyl-2-azaalanyl-1-acetic acid benzyl ester

Step A — Preparation of benzyl 1-lactate

A solution of crystalline 1-(+)-lactic acid (0.1 mole) in dry benzyl alcohol (46 ml) at 0°–5° is saturated with a slow stream of dry hydrogen chloride gas for 4 hours. The reaction solution is allowed to age at room temperature overnight with a drying tube. The solution is concentrated in vacuo and the residue is vacuum distilled to give benzyl 1-lactate (bp. 90°–91°/0.8–0.9 mm).

Step B — Preparation of acetylalanylalanylprolyl-2-azaalanyl-1-lactic acid benzyl ester Employing the procedure substantially as described in Example 1, but substituting for the ethyl 1-(+)-lactate used in Step A thereof, an equivalent amount of benzyl 1-lactate, there are prepared in sequence, Step A — (1-benzyloxycarbonyl)-ethyl chloroformate
Step B — 2-azaalanyl-1-lactic acid benzyl ester.
Step C — acetylalanylalanylprolyl-2-azaalanyl-1-lactic acid benzyl ester.

EXAMPLE 10

Acetylalanylalanylprolyl-2-azaalanyl-1-lactic acid

Acetylalanylalanylprolyl-2-azaalanyl-1-lactic acid benzyl ester (2.4 mmole) is dissolved in 2BA (denaturated ethyl alcohol, Formula 2B, 0.5 gal. benzene added to 100 gal. of 95% ethanol) (60 ml) and hydrogenated over 10% palladium-charcoal (0.13 gm) at 40 psi for ½ hour. The mixture is filtered through celite and evaporated in vacuo. Trituration of the residue with ether gives acetylalanylalanylprolyl-2-azaalanyl-1-lactic acid.

EXAMPLE 11

Acetylalanylalanylprolyl-2-azaalanyl-1-lactyl-phenylalanine-ethyl ester

Acetylalanylalanylprolyl-2-azaalanyl-1-acetic acid (0.15 mmole) is dissolved in methylene chloride (6 ml) containing N-methylmorpholine (3 mmole) and diluted with dry tetrahydrofuran (200 ml). To this stirred solution at −20° to −25° is added isobutyl chloroformate (.15 mmole) and the mixture is stirred for 10 minutes. A cold suspension of phenylalanine ethyl ester hydrochloride (0.15 mmole) in tetrahydrofuran (80 ml) containing N-methylmorpholine (0.15 mmole) is added in portions.

The mixture is allowed to warm to room temperature over a period of three hours and stirred overnight. The mixture is filtered, and the filtrate is evaporated to dryness. Chromatography of the residue on a silica gel (40 gm) and elution with 10% methanol in chloroform gives acetylalanylalanylprolyl-2-azaalanyl-1-lactylphenylalanine ethyl ester.

EXAMPLE 12

Acetylalanylalanylprolyl-2-azaalanyl-1-lactic acid p-iodobenzyl ester

Step A — Preparation of p-iodobenzyl alcohol

To a stirred solution of p-iodobenzoic acid (5 mmole) in a dry tetrahydrofuran (20 ml) at −70° is added a suspension of lithium aluminum hydride (10 mmole) in tetrahydrofuran (10 ml). The mixture is allowed to warm to 0° and stirred at 0° for 2 hours. The reaction mixture is then poured into a dilute hydrochloric acid — ice mixture and extracted with ether. The ether extract is washed with dilute bicarbonate solution, washed, dried over sodium sulfate and concentrated to dryness. Chromatography of the residue on a silica gel gives p-iodobenzyl alcohol.

Step B — Preparation of acetylalanylalanylprolyl-2-azaalanyl-1-lactic acid p-iodobenzyl ester Acetylalanylalanylprolyl-2-azaalanyl-1-lactic acid (0.2 mmole) and dicyclohexylcarbodiimide (0.11 mole) are suspended in acetonitrile (2 ml) and diluted with methylene chloride (6 ml). The mixture is stirred at room temperature for 1 hour and filtered. The filtrate is concentrated to dryness to give acetylalanylalanylprolyl-2-azaalanyl-1-lactic acid anhydride. The generated anhydride and p-iodobenzyl alcohol (0.1 mmole) are dissolved in pyridine (0.5 ml). The mixture is heated on a steam bath for ½ hour and concentrated to dryness. Purification via preparative thin-layer chromatography on silica gel, there is produced acetylalanylalanylprolyl-2-azaalanyl-1-lactic acid p-iodobenzyl ester.

EXAMPLE 13

Acetylalanylalanylprolyl-2-azaalanyl-N-benzyl-1-lactamide

Acetylalanylalanylprolyl-2-azaalanyl-1-lactic acid (0.5 mole) and dicyclohexylcarbodiimide (0.30 mole) are suspended in acetonitrile (5 ml) and diluted with methylene chloride (15 ml). After stirring at room temperature for 1 hour, benzylamine (0.5 mmole) is added. The mixture is allowed to stir at room temperature overnight and concentrated to dryness. Chromatography on preparative thin-layer silica gel and development with 20% methanol in chloroform gives acetylalanylalanylprolyl-2-azaalanyl-N-benzyl-1-lactamide.

EXAMPLE 14

Acetylalanylalanylprolyl-2-azaalanyl-N-methyl-1-lactamide

Following the procedure of Example 11, but substituting for the phenylalanine ethyl ester hydrochloride used therein, an equivalent amount of methylamine hydrochloride, there is prepared acetylalanylalanylprolyl-2-azaalanyl-N-methyl-1-lactamide.

EXAMPLE 15

Acetylalanylalanylprolyl-2-azaalanyl-1-lacthydrazide

Step A — Preparation of anhydrous hydrazine in tetrahydrofuran solution

Hydrazine hydrate (5.0 gm) is covered with dry tetrahydrofuran (100 ml) in the presence of sodium hydroxide (5.0 gm) with stirring for 1 hour. The solution is decanted and dried over new sodium (5.0 gm).

Step B — Preparation of acetylalanylalanylprolyl-2-azaalanyl-1-lacthydrazide

Following the procedure of Example 11, but substituting for the ethyl phenylalaninate hydrochloride used therein, an excess amount of anhydrous hydrazine in tetrahydrofuran there is prepared acetylalanylalanylprolyl-2-azaalanyl-1-lacthydrazide.

EXAMPLE 16

Acetylalanylalanylprolyl-2-azaalanyl-N-phenyl-1-lactamide

Following the procedure of Example 13, but substituting for the benzylamine used therein, an equivalent amount of aniline, there is produced acetylalanylalanylprolyl-2-azaalanyl-N-phenyl-1-lactamide.

EXAMPLE 17

Acetylprolylalanylprolyl-2-azaalanyllactyllactic acid ethyl ester

Step A — 2-Azaalanyllactyllactic acid ethyl ester

To a mixture of 50 ml of 12.5% phosgene in benzene and 50 ml of tetrahydrofuran which has been cooled to 0° to +5° is added slowly a mixture of 0.05 mole of ethyl lactyllactate and 0.05 mole of triethylamine in 50 of tetrahydrofuran. The above reaction mixture is stirred at 0° to +5° for 2 hours and is then added dropwise to a mixture of 3 gm of methylhydrazine and 0.05 moles of triethylamine in 50 ml of tetrahydrofuran which has been cooled to 0° to +5°. After stirring for 3 hours the reaction mixture is filtered to remove triethylamine hydrochloride. The filtrate is then concentrated in vacuo to give 13.6 gm of crude product. Chromatography on 700 gm of silica gel and elution with methanol/methylene chloride give 6.9 gm of 2-azaalanyllactyllactic acid ethyl ester.

Step B — Acetylprolylalanylprolyl-2-azaalanyllactyllactic acid ethyl ester.

A mixture of 0.00185 moles of acetylprolylalanylproline and 0.20 ml of N-methylmorpholine in 20 ml of acetonitrile is cooled to −20° by means of a Dry Ice acetone bath. To this is added 0.28 ml of isobutyl chloroformate. After stirring for 10 minutes at −20° there is added 0.00185 moles of 2-azaalanyllactyllactic acid ethyl ester in 5 ml of acetonitrile. The reaction mixture is allowed to warm to room temperature after which it is stirred for 2 hours and then concentrated in vacuo. The residue is extracted between 50 ml of methylene chloride and 20 ml of cold 0.25 N hydrochloric acid. The acid layer is backwashed 2 times with 25 ml of methylene chloride. The organic extracts are combined, dried over sodium sulfate and concentrated in vacuo to give a glass. This residue is chromatographed on 75 gm of silica gel. Elution with methanol/methylene chloride (1-4%) gives pure acetylprolylalanylprolyl-2-azaalanyllactyllactic acid ethyl ester.

EXAMPLE 18

Acetylalanylalanylprolyl-2-azaalanyllacetyllactic acid ethyl ester

When acetylalanylalanylproline is used in place of acetylprolylalanylpropline in the procedure of Example 17 there is obtained acetylalanylalanylprolyl-2-azaalanyllactyllactic acid ethyl ester.

EXAMPLE 19

Acetylprolylalanylprolyl-2-azavalyl-1-lactic acid ethyl ester

N-Methylhydrazine in 1B above is replaced by N-isopropylhydrazine to give 2-azavalyl-1-lactic acid ethyl ester, and 2-azaalanyl-1-lactic acid ethyl ester in 1C above is replaced by 2-azavalyl-1-lactic acid ethyl ester to give acetylprolylalanylprolyl-2-azavalyl-1-lactic acid ethyl ester.

EXAMPLE 20

5-Amino-1-ethoxycarbonylpentyl Acetylproylalanylprolyl-2-azaalaninate Hydrochloride

Step A — Ethyl 6-Amino-2-hydroxyhexanoate Hydrochloride

A solution of 0.1 mole of 6-amino-2-hydroxyhexanoic acid in 150 ml of anhydrous ethanol is saturated with dry hydrogen chloride gas and is stirred overnight at room temperature. The reaction mixture is then concentrated in vacuo to give ethyl 6-amino-2-hydroxyhexanoate hydrochloride.

Step B — Ethyl 6-(Benzyloxycarbonylamino)-2-hydroxyhexanoate

To a well stirred mixture of 0.05 moles of ethyl 6-amino-2-hydroxyhexanoate and 100 ml of methylene chloride which has been cooled to 0° to 5° C is added 0.1 moles of N-methylmorpholine followed by 0.055 moles of carbobenzoxy chloride. The reaction mixture is stirred for 1 hour then washed with saturated sodium bicarbonate solution. The organic layer is dried over sodium sulfate and concentrated in vacuo. Chromatography of the residue on silica gel and elution with methanol/chloroform gives ethyl 6-(benzyloxycarbonylamino)-2-hydroxyhexanoate.

Step C — 1-Ethoxycarbonyl-5-benzyloxycarbonylaminopentyl chloroformate

Following the procedure of Example 1, Step A, but substituting for the ethyl lactate therein, an equivalent amount of ethyl 6-benzyloxycarbonylamino-2-hydroxyhexanoate, there is produced 1-ethoxycarbonyl-5-benzyloxycarbonylaminopentyl chloroformate.

Step D — 1-Ethoxycarbonyl-5-benzyloxycarbonylaminopentyl 2-azaalaninate

Following the procedure of Example 1, Step B, but substituting for the 1-ethoxycarbonylethyl chloroformate therein, an equivalent amount of 1-ethoxycarbonyl-5-benzyloxycarbonylaminopentyl chloroformate, there is produced 1-ethoxycarbonyl-5-benzyloxycarbonylaminopentyl 2-azaalaninate.

Step E — 5-Benzyloxycarbonylamino-1-ethoxycarbonylpentyl acetylprolylalanylprolyl-2-azaalaninate Following the procedure of Example 1, Step C, but substituting for the 2-azaalanyl-1-lactic acid ethyl ester therein, an equivalent amount of 1-ethoxycarbonyl-5-benzyloxycarbonylaminopentyl 2-azaalaninate, there is produced 5-benzyloxycarbonylamino-1-ethoxycarbonylpentyl acetylprolylalanylprolyl-2-azaalaninate.

Step F — 5-Amino-1-ethoxycarbonylpentyl acetylprolylalanylprolyl-2-azaalaninate hydrochloride A mixture of 0.01 moles of 5-benzyloxycarbonylamino1-ethoxycarbonylpentyl acetylprolylalanylprolyl-2-azaalaninate and 0.2 gm of 10% Pd/C in 200 ml of 1.0 N-ethanolic hydrogen chloride is hydrogenated at room temperature. When the required amount of hydrogen has been taken up the reaction mixture is filtered and concentrated in vacuo to give 5-amino-1-ethoxycarbonylpentyl acetylprolylalanylprolyl-2-azaalaninate hydrochloride.

EXAMPLE 21

PARENTERAL FORMULATIONS

Step A — Preconstituted Solutions

AAAL*: 50 mg
Sodium chloride: 9.0 mg
NaOH or HCl: q.s. to pH 5-6
Water for Injection: q.s. 1.0 ml

*AAAL is an abbreviation used for acetylalanylalanylprolyl-2-azaalyanyl-dl-lacthydrazide.

Other concentrations of preconstituted solutions of AAAL cover the range of 5-250 mg/ml as required for therapy. Suitable buffering agents such as citric acid, sodium phosphate, TRIS, and the like may be added to the above compositions. Additionally, other pharmaceutical adjuvants such as antioxidants, chelating agents commonly employed in the formulation of parenteral formulations may be added to enhance the stability and pharmaceutical elegance of the compositions noted above. Compositions may also contain benzyl alcohol (9 mg per ml) or methylparaben and propylparaben (1.5 mg/ml and 0.2 mg/ml).

Preconstituted solutions of AAAL are prepared by dissolving the ingredients in water for injection, adjusting the pH of the solutions to 5-6 and diluting to volume. The solutions are rendered sterile by absolute filtration and aseptically subdivided into sterile containers.

Step B — Cryodessicated AAAL

AAAL: 50 mg
Mannitol: 50 mg
NaOH or HCl: q.s. to pH 5-6
Water for Injection: q.s. 1.0 ml Compositions noted above may contain phenylmercuric acetate 0.1% as a preservative. Cryodessicated AAAL formulations are prepared by dissolving the ingredients and rendering the solution sterile by absolute filtration. Aliquots of the sterile solution are aseptically transferred to sterile vials. The vials are transferred to a freeze dryer and processed in the usual fashion. Other cryodessicated potencies of AAAL range from 5 to 250 mg per vial as required for therapy.

Similarly, an equivalent amount of acetylprolylalanylprolyl-2-azaalanyl-dl-lactamide, acetylalanylalanylprolyl-2-azaalanyl-dl-lactamide, acetylalanylalanylprolyl-2-azaalanyl-1lactic acid benzyl ester, acetylalanylalanylprolyl-2-azaalanyl-1-lactic acid p-iodobenzyl ester, acetylalanylalanylprolyl-2-azaalanyl-N-benzyl-1-lactamide, acetylalanylalanylprolyl-2-azaalanyl-N-methyl-1-lactamide, acetylalanylalanylprolyl-2-azaalanyl-1-lacthydrazide or acetylalanylalanylprolyl-2-azaalanyl-N-phenyl-1-lactamide may be substituted for the acetylalanylalanylprolyl-2-azaalanyl-dl-lacthydrazide (AAAL) in the above pharmaceutical compositions.

EXAMPLE 22

INHALATION AEROSOLS

EXAMPLE A

Suspensions of AAAL having a target metered delivery of 10 mg of drug per activation.
AAAL: 10 mg
Freon 11: 2.65 mg
Freon 12/114 (80–20 mixture): 57.35 gm
Microfine AAAL, having a particle size of less that 10 microns is uniformly dispersed in a mixture of the propellents. The suspension is then subdivided by standard "cold-fill" techniques into a suitable aerosol container system.

EXAMPLE B

Suspension of AAAL having a target metered delivery of 10 mg of drug per activation.
AAAL: 10 mg
Anhydrous Ethanol: 2.65 mg
Freon 12/114 (80–20 mixture): 57.35 gm
Preparation as noted above. It is recognized that other inert adjuvants used for the formulation of inhalation aerosols may be added to the compositions noted above.

EXAMPLE C

AAAL Powder For Inhalation

AAAL: 10 mg (range 1–25 mg)
Lactose: 90 mg (range 75–99 mg)
A uniform mixture of microfine AAAL and lactose are dispersed in conventional oral inhalation devices such as powder insufflators, Turbo-Inhaler (Fisons Corp.) and the like.

EXAMPLE D

AAAL Solution for Oral Inhalation

AAAL: 10 mg (range 1–25 mg)
HCl or NaOH: q.s. to pH 5–6
Water: q.s. to 1.0 ml
The preconstituted or extemporaneously prepared solutions described above may contain suitable solvents such as propylene glycol and ethanol to reduce surface tension, as well as other adjuvants commonly used in the preparation of solutions for nebulization.

Similarly, an equivalent amount of acetylprolylalanylprolyl-2-azzaalanyl-dl-lactamide, acetylalanylalanylprolyl-2-azalanyl-dl-lactamide, acetylalanylalanylprolyl-2-azaalanyl-1-lactic acid benzyl ester, acetylalanylalanylprolyl-2-azaalanyl-1-lactic acid p-iodobenzyl ester, acetylalanylalanylprolyl-2azaalanyl-N-benzyl-1-lactamide, acetylalanylalanylprolyl-2-azaalanyl-N-methyl-1-lactamide, acetylalanylalanylprolyl-2-azaalanyl-1-lacthydrazide or acetylalanylalanylprolyl-2-azaalanyl-N-phenyl-1-lactamide may be substittued for the acetylalanylalanylprolyl-2-azaalanyl-dl-lacthydrazide (AAAL) in the above pharmaceutical compositions.

What is claimed is:

1. A compound of the formula:

$$B-P_4-P_3-P_2-NH-\underset{R_1}{N}-\overset{O}{\underset{\|}{C}}-O-\underset{R_2}{CH}-\overset{O}{\underset{\|}{C}}-R_3 \qquad I$$

wherein
B is $C_{1-5}$alkanoyl, t-butoxycarbonyl or carbobenzyloxy,
$P_4$ is alanyl or prolyl,
$P_3$ is alanyl,
$P_2$ is prolyl or leucyl,
$R_1$ is $C_{1-5}$alkyl,
$R_2$ is methyl, benzyl or 4-aminobutyl, and
$R_3$ is hydroxy, $C_{1-5}$Alkoxy, amino, N-$C_{1-5}$alkylamino, N,N-di-($C_{1-5}$alkyl)amino, N-benzylamino, N-phenylamino, hydrazino, methylhydrazino, ethylhydrazino, phenylhydrazino, benzylhydrazino, benzyloxy, or p-iodobenzyloxy or $$-Z-\underset{R_4}{CH}-\overset{O}{\underset{\|}{C}}-R_5$$

wherein
$R_4$ is methyl or benzyl, and
$R_5$ is hydroxy, $C_{1-5}$alkoxy, amino, N-$C_{1-5}$alkylamino, N,N-di-($C_{1-5}$alkyl)amino, N-benzylamino, N-phenylamino, hydrazino, benzyloxy, or p-iodobenzyloxy and
Z is -NH- or —O—.

2. The compound of claim 1 wherein
B is $C_{1-5}$alkanoyl, $R_1$ is methyl or isopropyl, $R_2$ is methyl or benzyl, and $R_3$ is $C_{1-5}$alkoxy, benzyloxy, p-iodobenzyloxy, amino, hydrazino, N-phenylamino, N-benzylamino or $C_{1-5}$-alkylamino.

3. The compound of claim 2 wherein
B is acetyl,
$P_2$ is prolyl,
$R_1$ is methyl, $R_2$ is methyl, and
$R_3$ is benzyloxy, p-iodobenylzoxy, amino, hydrazino, N-phenylamino, N-benzylamino or N-methylamino.

4. The compound of claim 3 wherein $P_4$ is alanyl.

5. The compound of claim 3 wherein $P_4$ is prolyl.

6. Acetylprolylalanylprolyl-2-azaalanyl-di-lacthydrazide according to claim 5.

7. Acetylprolylalanylprolyl-2-azaalanyl-di-lactamide according to claim 5.

8. Acetylalanylalanylprolyl-2-azaalanyl-di-lactamide according to claim 5.

9. A pharmaceutical composition comprising a non-toxic pharmaceutically acceptable carrier and a therapeutically effective amount of a compound of the formula:

$$B-P_4-P_3-P_2-NH-\underset{R_1}{N}-\overset{O}{\underset{\|}{C}}-O-\underset{R_2}{CH}-\overset{O}{\underset{\|}{C}}-R_3 \qquad I$$

wherein

B is $C_{1-5}$alkanoyl, t-butoxycarbonyl or carbobenzyloxy, $P_4$ is alanyl or prolyl, $P_3$ is alanyl, $P_2$ is prolyl or leucyl, $R_1$ is $C_{1-5}$alkyl, $R_2$ is methyl, benzyl or 4-aminobutyl, and $R_3$ is hydroxy, $C_{1-5}$alkoxy, amino, N-$C_{1-5}$alkylamino, N-benzylamino, N-phenylamino, hydrazino, methylhydrazino, ethylhydrazino, phenylhydrazino, benzylhydrazino, benzyloxy, or

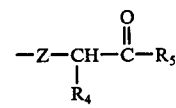

wherein $R_4$ is methyl or benzyl, and $R_5$ is hydroxy, $C_{1-5}$alkoxy, amino, N-$C_{1-5}$alkylamino, N-benzylamino, N-phenylamino, hydrazino, benzyloxy, or p-iodobenzyloxy and Z is —NH— or —O—.

* * * * *